United States Patent [19]

Hoffman

[11] 4,418,647

[45] Dec. 6, 1983

[54] ARTIFICIAL HOST EGG FOR REARING TRICHOGRAMMA

[75] Inventor: Jarett D. Hoffman, Columbia, Mo.

[73] Assignee: The United States of America as represented by the Secretary of Agriculture, Washington, D.C.

[21] Appl. No.: 380,375

[22] Filed: May 20, 1982

[51] Int. Cl.³ .............................................. A01K 67/00
[52] U.S. Cl. ........................................... 119/1; 119/15
[58] Field of Search ...................................... 119/1, 15

[56] References Cited

U.S. PATENT DOCUMENTS

| 3,750,625 | 8/1973 | Edwards | 119/1 |
| 3,893,420 | 7/1975 | Andreev et al. | 119/1 |
| 3,941,089 | 3/1976 | Andreev et al. | 119/1 |
| 4,370,946 | 2/1983 | Voegele et al. | 119/1 |

Primary Examiner—Hugh R. Chamblee
Attorney, Agent, or Firm—M. Howard Silverstein; David G. McConnell; Curtis P. Ribando

[57] ABSTRACT

Trichogramma are reared in vitro on an artificial membrane having a curvilinear surface region, the outer convex surface of which is adapted to induce oviposition by the adult wasps, and the inner concave surface of which defines a cavity adapted for recovery of the oviposited eggs.

9 Claims, 5 Drawing Figures

ARTIFICIAL HOST EGG FOR REARING TRICHOGRAMMA

BACKGROUND OF THE INVENTION

1. Field of the Invention

The genus Trichogramma represents a vast array of endoparasitic species of minute wasps found in diverse habitats throughout the world. Their life cycle initiates with the adult female wasp ovipositing eggs into the eggs of a host insect. Hatching larvae feed on the host egg, pupate, and emerge within approximately 10 days of oviposition as mature adult parasites. These parasites are commercially reared and released in many countries for use as biological control agents against a plurality of agricultural pests, particularly those which attack economically important food and fiber crops.

All existing programs for mass rearing Trichogramma depend upon providing an ample supply of viable host eggs. As a result of the several handling steps and the requirement for fairly elaborate facilities, host egg production accounts for more than 90% of the rearing costs. It is envisioned that a substantial reduction in the overhead attributed to maintaining a host population would greatly enhance the role of Trichogramma in the control of agricultural pests. This invention relates to a cultivation method by which such a cost reduction can be realized.

2. Description of the Prior Art

The conventional procedure for propagating Trichogramma initiates with production and collection of an abundance of host eggs such as those of the Angoumois grain moth. The collected eggs are enchambered with a predetermined number of parasitized eggs so that the emerging wasps will infest the remainder of the lot. The infested eggs may either be refrigerated to retard hatching or else directly transferred to an incubation chamber for further development. Release of adult parasites typically occurs prior to or immediately after emergence. Because of the manual handling of both the host and the parasite, this procedure is unduly labor intensive and economically unfeasible.

Attempts to improve upon the conventional technique have centered upon optimization of conditions, automation, and implementation of a continuous flow principle from one stage to the next. For example, Andreev et al., U.S. Pat. No. 3,893,420 teaches a method wherein host eggs are collected by a pneumatic separator and are attached in symmetrical arrays on uniformly sized cards for subsequent transfer to each rearing station. While the method of Andreev et al. facilitates the production and handling of the eggs, it does little to offset the expense of concurrently rearing the host.

SUMMARY OF THE INVENTION

We have now discovered a system for use in the in vitro rearing of Trichogramma, thereby obviating the need for a natural host egg. The system employs a substrate comprising an artificial membrane having a curvilinear surface and adapted to induce oviposition by mature female wasps. Development of the oviposited eggs to adults is thereafter accomplished on a suitable nutrient medium which is either underlying the membrane or else located in a remote rearing facility.

In accordance with this discovery, it is an object of the invention to provide an efficient and economical system for the large-scale production of Trichogramma.

It is also an object of the invention to produce an artificial membrane which is conducive to the oviposition therein by mature Trichogramma females.

A further object of the invention is to rear Trichogramma in a manner which facilitates their recovery for mass release into the environment.

Other objects and advantages of the invention will become readily apparent from the ensuing description.

DETAILED DESCRIPTION OF THE INVENTION

Figure 1:
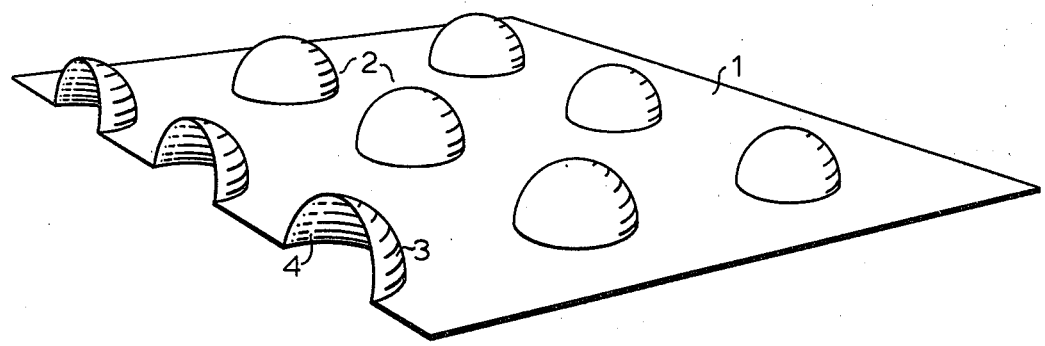
FIG. 1 is a perspective view of one embodiment of the invention in which the curvilinear surface regions are hemispherical.

Referring to FIG. 1, the artificial substrate of the invention comprises a membranous material 1 which has been shaped to incorporate one or more curvilinear surface regions 2 characterized by an outer convex surface 3 and an inner concave surface 4. The membrane, particularly that of the curvilinear surface regions should have a combination of thickness, strength, and hardness such that it will retain its shape and will also be penetratable by the ovipositor of the Trichogramma species being reared. Common polymeric film formers such as paraffin, calcium alginate, polyethylene, polypropylene, "Parafilm" and the like are illustrative of suitable materials, though determination of others meeting the aforementioned criteria would be within the ambit of the skilled artisan. Typically, the thickness of the membrane will be in the range of approximately 1–100$\mu$, and more preferably about 10–20$\mu$, depending on the material selected. In the curvilinear regions 2, the texture of the outer surface of the membrane should be sufficiently textured to facilitate grasping with the tarsal claws of the adult female parasite during oviposition. When polypropylene film is stretched beyond its yield point, it not only obtains an acceptable thickness, but also develops microscopic striations which provide a firm footing for the wasps. The curvilinear surface regions should extend through an arc of at least 90° and have a radius of curvature in the range of about 0.1 to 3.0 mm., and preferably 0.2 to 1 mm.

Figure 2:
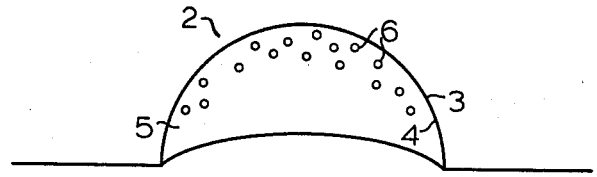
FIG. 2 is a sectional view of one of the curvilinear surface regions of FIG. 1 in one mode of application.

Referring to FIG. 2, the inner surface 4 of the region 2 defines a semienclosed cavity which has sufficient access from the inner surface side of the membrane to enable flushing as discussed further below. The cavity is adapted to receive, and to hold in contact with the inner surface 4, an inducement medium 5 for further enhancing oviposition.

Figure 3:
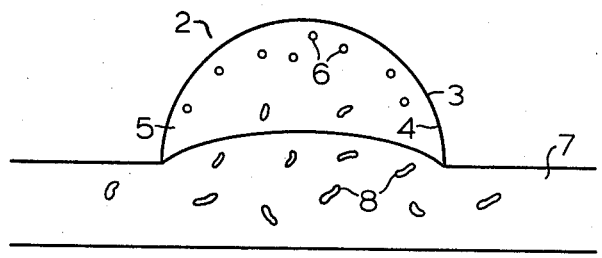
FIG. 3 is a sectional view of one of the curvilinear surface regions of FIG. 1 in another mode of application.

Eggs 6 oviposited by adult female wasps at the sites of the curvilinear surface regions are readily recovered by flushing the inducement medium and entrained eggs from the inner membrane surface. They are thereafter transferred to a nutrient medium for further development. Prior to transfer, the eggs may be separated from the inducement medium by filtration or other conventional separatory method. Upon addition of a nutrient, larvae can be reared directly on the filter paper used to recover the eggs. As shown in FIG. 3, the nutrient medium 7 may underly the membrane 1 for in situ rearing of larvae 8 without transfer to a separate facility. Of course it would be appreciated by the skilled artisan that for either in situ or remote rearing, the inducement and nutrient media can be combined as a single dual-purpose medium. While specific media formulations are outside the scope of this invention, both host egg homogenate and dilute insect homolymph are effective for these purposes. Artificial inducement media and artificial diets are also envisioned for use in the in vitro system.

Figure 4:
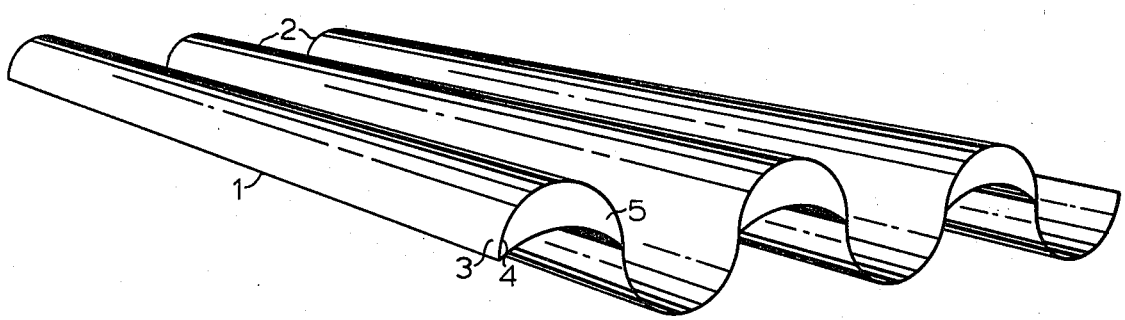
FIG. 4 is a perspective view of an alternate embodiment of the invention in which the curvilinear surface regions are ripple-shaped.

FIG. 4 depicts an alternate embodiment for the configuration of the curvilinear surface regions. The convex outer surfaces 3 are the crests of sinusidal ripples or undulations in the membrane 1. Sheets of polymeric films can be rippled in such a manner by slightly biasing opposing edges.

Figure 5:
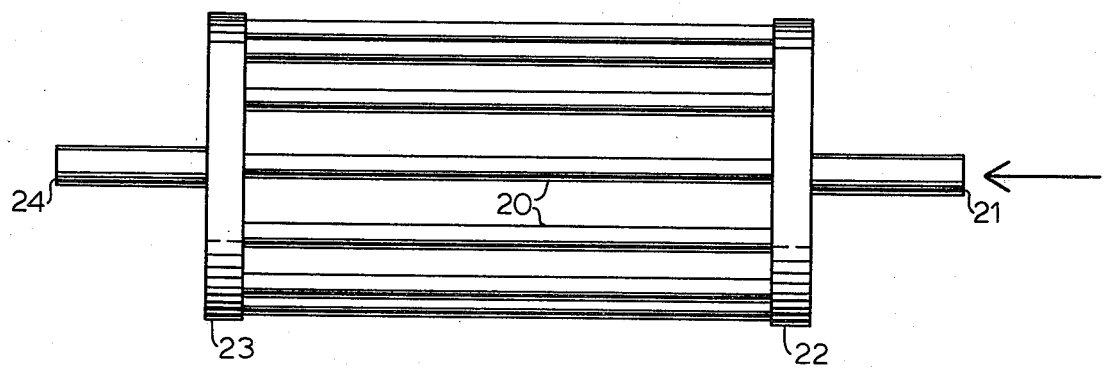
FIG. 5 is a plan view of an alternate embodiment of the invention in which the curvilinear surface regions are tubular.

FIG. 5 illustrates a third embodiment of the invention specifically adapted for the continuous transfer of oviposited eggs to a nutrient medium in a remote rearing facility. Membranous tubules 20 are characterized by a cylindrically shaped convex outer surface. An intermittent or continuous flow of inducement nutrient is maintained through the tubules by means of inlet 21, headers 22 and 23, and outlet 24. Upon recovery of the eggs, the medium can be recirculated to inlet 21. Alternatively, the system is adaptable to a single-pass operation in which a combined dual-purpose medium entrains oviposited eggs from the tubular cavities and is thereafter directed to a rearing chamber.

It is understood that the foregoing detailed description is given merely by way of illustration and that modification and variations may be made therein without departing from the spirit and scope of the invention.

I claim:

1. A substrate for use in the in vitro rearing of Trichogramma wasps and adapted for oviposition therein by mature females, said substrate comprising an artificial membrane having an outer surface and an inner surface and at least one curvilinear surface region extending through an arc of at least about 90°, said region being convex on the outer surface of said membrane and concave on the inner surface of said membrane, wherein the membrane in said region is characterized by a thickness, curvature, and outer surface texture suitable to induce oviposition by said females, and wherein the membrane on the inner surface of said region defines a semienclosed cavity.

2. The substrate as described in claim 1 wherein said curvilinear surface region is hemispherical.

3. The substrate as described in claim 1 wherein said curvilinear surface region is the crest of a ripple.

4. The substrate as described in claim 1 wherein said curvilinear surface region is tubular.

5. The substrate as described in claim 1 wherein the radius of curvature of said membrane in the curvilinear surface region is in the range of about 0.1 to about 3.0 mm.

6. The substrate as described in claim 1 further comprising an inducement medium within said semienclosed cavity and in contact with the inner surface of said membrane.

7. A method for the in vitro rearing of Trichogramma wasps by means of a substrate comprising: (1) an artificial membrane having an outer surface and an inner surface and at least one curvilinear surface region extending through an arc of at least about 90°, said region being convex on the outer surface of said membrane and concave on the inner surface of said membrane, wherein the membrane in said region is characterized by a thickness, curvature, and outer surface texture suitable to induce oviposition by the females of said wasps, and wherein the membrane on the inner surface of said region defines a semienclosed cavity; and (2) an inducement medium within said cavity and in contact with the inner surface of said membrane; said method comprising:

a. introducing adult Trichogramma wasps to said outer surface whereby females of said wasps will be induced to penetrate the membrane in said curvilinear surface region and to oviposit eggs into said inducement medium;

b. providing a nutrient medium to Trichogramma larvae hatching from said eggs; and c. rearing Trichogramma in said nutrient medium.

8. The method as described in claim 7 wherein said nutrient medium is formulated in combination with said inducement medium and said Trichogramma are reared adjacent to the inner surface of said membrane.

9. The method as described in claim 7 wherein said nutrient medium is distinct from said inducement medium and said oviposited eggs from step (a) are transferred to said nutrient medium prior to further rearing.

* * * * *